(12) United States Patent
Anevski

(10) Patent No.: US 6,388,112 B1
(45) Date of Patent: May 14, 2002

(54) PROCESS FOR PURIFICATION OF SOLVENTS USEFUL IN THE PREPARATION OF PHARMACEUTICAL COMPOSITIONS

(75) Inventor: Phillip J. Anevski, St. Louis, MO (US)

(73) Assignee: Ben Venue Laboratories, Inc., Bedford, OH (US)

( * ) Notice: Subject to any disclaimer, the term of this patent is extended or adjusted under 35 U.S.C. 154(b) by 0 days.

(21) Appl. No.: 09/807,046

(22) PCT Filed: Oct. 20, 1999

(86) PCT No.: PCT/US99/24552

§ 371 Date: Apr. 6, 2001

§ 102(e) Date: Apr. 6, 2001

(87) PCT Pub. No.: WO00/23070

PCT Pub. Date: Apr. 27, 2000

Related U.S. Application Data

(60) Provisional application No. 60/104,930, filed on Oct. 20, 1998.

(51) Int. Cl.⁷ .................................................. C11B 3/10
(52) U.S. Cl. ....................................... 554/191; 514/552
(58) Field of Search ........................... 554/191; 514/552

(56) References Cited

U.S. PATENT DOCUMENTS

| 5,403,858 A | 4/1995 | Bastard et al. |
| 5,504,102 A | 4/1996 | Agharkar et al. |
| 5,733,888 A | 3/1998 | Carver et al. |
| 5,925,776 A | 7/1999 | Nikolayev et al. |
| 5,972,992 A | 10/1999 | Carver et al. |
| 5,977,164 A | 11/1999 | Carver et al. |
| 6,096,911 A | 4/2000 | Dralle-Voss et al. |
| 6,140,359 A | 10/2000 | Carver et al. |

FOREIGN PATENT DOCUMENTS

EP           645145        *  3/1993

* cited by examiner

*Primary Examiner*—Deborah D. Carr
(74) *Attorney, Agent, or Firm*—Watts Hoffman Fisher & Heinke

(57) ABSTRACT

A process for purifying a non-ionic surfactant or solvent capable of dispersing and solubilizing a pharmaceutical compound. In the process, a solution of solvent and alcohol is contacted with an activated carbon column and an ion exchange resin column. The process is particularly adapted to the purification of polyethoxylated castor oils. The purified solvent is useful in the preparation of pharmaceutic compositions having enhance shelf life, such as for use with paclitaxel.

28 Claims, No Drawings

PROCESS FOR PURIFICATION OF SOLVENTS USEFUL IN THE PREPARATION OF PHARMACEUTICAL COMPOSITIONS

This application is a 371 of PCT/059a/24552 filed Oct. 20, 1999, and claims the benefit of Ser. No. 60/,104,930 filed Oct. 20, 1998.

FIELD OF THE INVENTION

The present invention is directed to a process for purifying a solvent suitable for use with a pharmaceutical agent and to the purified solvent and pharmaceutical compositions prepared therewith.

BACKGROUND OF THE INVENTION

Administration of pharmaceutical compounds, and in particular administration by injection, requires a solvent or carrier that is suitable for administration to the patient. The solvent used in conjunction with the pharmaceutical agent must, when combined with the pharmaceutical agent, produce an effective composition for injection, ideally having good shelf life. The solvent should be non-toxic to the patient and compatible with the particular pharmaceutical agent to be injected. Many solvents are not especially efficient for solubilizing the pharmaceutical agent to enable an effective composition for administration, while simultaneously possessing these advantageous qualities.

Compositions containing polyethoxylated castor oil and similar solvents are frequently used in combination with a pharmaceutical agent to produce a mixture suitable for administration by injection. The solvents acceptable for pharmaceutical use are set forth in a United States Pharmacopoeia (USP) with the acceptable limits for various parameters of these solvents in a National Formulary (NF). A potential problem associated with such solvents is that acids, salts or other ionic impurities, as well as residual water in the solvent or solvent system, even if within the acceptable limits, can catalyze the degradation of the pharmaceutical agent. For example, it is believed that carboxylate anions present in polyethoxylated castor oil can catalyze the decomposition of paciltaxel, even at levels within the defined limits set forth in the National Formulary. See, for example, U.S. Pat. No. 5,504,102, incorporated herein by reference. The U.S. Pat. No. 5,504,201 patent discloses removing the carboxylate anions from polyethoxylated castor oils by acid addition or alumina adsorption. A solvent with sufficiently low levels of particular deleterious impurities will yield a more stable pharmaceutical agent containing compositions.

Because such solvents and solvent systems are combined with pharmaceuticals used in the treatment of, among other things, cancer, the importance of developing a method for removing impurities that deleteriously effect the stability of the pharmaceutical agent is apparent. There is a need for the development of a solvent or cosolvent system that does not negatively impact the potency or purity of the pharmaceutical agent and which provides for good shelf life. The present invention addresses the problems of loss of effectiveness of the pharmaceutical agent due to decomposition during storage. Moreover, the present invention does not affect the pH during purification of the solvent

SUMMARY OF THE INVENTION

The present invention provides a process for purifying a solvent for use in the formulation of a pharmaceutical agent composition. The invention also provides purified solvent produced by this process and a pharmaceutical composition comprising the purified solvent and a pharmaceutical agent, which composition has extended shelf-life. More particularly, the present invention is directed to an improved process for purifying a solvent which results in advantageously low quantities of salts, acids and various other ionic impurities, as well as low residual water content and enhanced clarity. In a preferred aspect of the invention, the process involves the purification of polyethoxylated castor oils, sometimes called polyoxyethylated castor oils, by forming a solution of the solvent in alcohol and contacting the solution with an activated carbon column, followed by contacting the solution with an ion exchange resin column and then evaporating the residual water and alcohol. The resin column follows the charcoal column in the preferred embodiment so that, in the event any charcoal particulates remain after the charcoal column, they will be eliminated by the resin column. While not wanting to be bound by theory, it is believed that contact with the activated carbon removes water and unsaturated aliphatic and aromatic compounds by an adsorption mechanism. The ion exchange resin is believed to exchange cations and anions from the solvent with OH– and H+.

The solvents that are purified are non-ionic surfactants. The solvent is preferably a condensation product of an alkylene oxide and an oil or fatty acid. The preferred solvent is a polyethoxylated castor oil, such as polyoxyl 35 castor oil, Cremophor RH60, or a similar solvent such as polysorbate 80. Still more preferably, the solvent is a polyoxyl 35 castor oil. Commercially available polyethoxylated castor oils to which the present process is particularly suited are sold under the trade name Cremophor, such as Cremophor EL and Cremophor RH60. In the present invention, the polyethoxylated castor oils such as Cremophor EL and Cremophor RH60 are treated to enhance clarity and reduce potassium, salt, acid, water content and other deleterious impurities.

It is another aspect of the present invention to provide purified polyethoxylated castor oils that, when employed to solubilize pharmaceutical agents, produce a pharmaceutical composition having an advantageously long shelf life.

In one embodiment, such as for purifying polyoxyl 35, the resulting, purified polyethoxylated castor oil has a specific gravity between 1.05 and 1.06 g/ml, a viscosity between 650 and 850 cps at 25° C. an acid value (NF) of not more than 2.0, a hydroxyl value (NF) between 65 and 80, a potassium content less than or-equal to 15 ppm, a water percentage less than about 3.0%, and preferably less than or equal to 0.5%, a saponification of between 60 and 75 and an iodine value (NF) of 25 to 35.

In another embodiment, such as for purifying polysorbate 80, the resulting, purified solvent has a specific gravity between 1.06 and 1.09 g/ml, a viscosity between 300 and 500 cps., an acid value (NF) of not more than 2.2, a hydroxyl value (NF) between 65 and 80, a water percentage less than about 3.0%, and preferably less than or equal to 0.5%, and a saponification of between 45 and 55. Polysorbate 80 is a non-ionic surfactant and can be generally classified as a polyol with a similar chemical structure to the polyethoxylated castor oils and is hereinafter generally referred to as a polyethoxylated castor oil.

In another embodiment, such as for purifying Cremophor RH60, the resulting, purified polyethoxylated castor oil has a specific gravity of about 1.1 g/ml, a viscosity of about 211 cps. at 60° C., an acid value (NF) less than 0.2, a hydroxyl value (NF) of about 69, an iodine value less than about 2, a water percentage of about 0.4%, a potassium value less than about 7 ppm, and a saponification of about 44.

The invention is also directed towards stabilized pharmaceutical compositions prepared from the solvent according to the invention. Preferred pharmaceutical compounds that may be combined with the solvent after purification include antineoplastic compounds such as teniposide, paclitaxel and camptothecin, immunosuppressive agents such as cyclosporin and tacrolimus, oil soluble vitamins, mixtures thereof and the like. A purified polyethoxylated castor oil having the preferred characteristics will produce a pharmaceutical composition having a good shelf life. In the preferred embodiment, the pharmaceutical agent is paclitaxel and the process is carried out so as to produce a polyethoxylated castor oil that, when combined with the paclitaxel in a pharmaceutical composition, will provide at least about 90% of the initial amount of paclitaxel after being stored at 40° C. for ninety days. Still more preferably, the composition will provide at least about 97%±5% paclitaxel after being stored at 40° C. for ninety days.

To obtain this product, the process employs respective amounts of activated carbon and ion exchange resin, and passes the polyethoxylated castor oil through the respective columns at rates suitable to produce a purified polyethoxylated castor oil having the desired properties. One of ordinary skill in the art will be able to empirically determine appropriate amounts of activated carbon and ion exchange resin, and suitable flow rates to obtain the desired product in view of the present disclosure. It will be apparent, for example, that a minimal amount of resin or carbon will be necessary to obtain the desired result and that an excess amount or volume may result in residence times on the column that are too long. Similarly, after a sufficiently long period of use, it is believed that the resin and/or charcoal will become spent, and no longer function to remove the necessary impurities efficiently. These limitations can obviously be empirically determined by those of ordinary skill in the art by assaying the product and determining whether it falls within the desired specifications.

Preferably, the invention employs activated charcoal in the carbon column at a ratio of 0.19 to 0.2 Kg of charcoal per Kg of polyethoxylated castor oil, and an ion exchange resin at a ratio of 0.21 to 0.22 Kg of resin per Kg of polyethoxylated castor oil. More preferably, the ion exchange resin is a mixed bed ion exchange resin for exchanging H+ and OH− for anions and cations present in the untreated solvent. At these ratios, the polyethoxylated castor oil is preferably passed through the carbon column at a rate of from about 0.16 to 0.22 column volumes per hour (cv/hr), and through the resin column at a rate that is no greater than about 0.30 cv/hr, and preferably between about 0.12 to about 0.30 cv/hr.

While not being bound by theory, it is believed that the critical parameter necessary to obtain the purified polyethoxylated castor oil having the desired characteristics is the time the unpurified oil spends on the respective columns. If the residence time is too short, then the columns will not remove sufficient amounts of impurities to provide the desired product. If the residence time is too long, then the column may remove desirable constituents and result in an unsuitable product. It is believed that this is particularly true for the carbon column. If the residence time on the charcoal column is too long, the amount of fatty acid component, which is indicated by the iodine value, may be adversely effected, resulting in an unsuitable product. The danger of removing desirable constituents from the treated solvent is believed to be less significant during contact with the ion exchange resin.

Residence time is a function of the amount or volume of resin or charcoal in the column and rate at which the oil is passed through the column, which may be indicated by column volumes per hour. Thus, according to the invention, if one increases the amount of, for example, charcoal in the column and hence the ratio of charcoal to polyethoxylated castor oil, then one should increase the rate at which the castor oil is run through the column accordingly, so that the actual residence time remains within acceptable parameters. With the preferred charcoal, approximately 8 Kg is used, making the column volume approximately 16 liters. Thus, at the preferred rate of 0.16 to 0.22 cv/hr, the residence time for the polyethoxylated castor oil on the column is about 2.6 to 4.8 liters per hour. Likewise, with the preferred resin, approximately 19 lbs. (8.6 Kg) yields a column volume of about 11 liters, such that the residence time of the polyethoxylated castor oil on the resin column is about 1.3 to 3.3 liters per hour at the preferred rate of 0.12 to 0.30 cv/hr.

The advantages of this invention are attained by producing this ultrapure polyethoxylated castor oil as a solvent or solubilizing agent for solubilizing pharmaceutical agents, thereby producing stabilized pharmaceutical compositions. The clarity is enhanced and the levels of deleterious impurities are lowered sufficiently to prevent degradation of pharmaceutical agents. The resulting pharmaceutical compositions can exhibit a high level of potency for prolonged periods of time.

DETAILED DESCRIPTION OF THE PREFERRED EMBODIMENTS

The preferred solvent to be purified according to the invention is a polyethoxylated castor oil. Still more preferably the solvent is a polyoxyl-35 castor oil. Polyethoxylated castor oils may be prepared according to methods known in the art, or obtained commercially. As noted, the polyoxyl-35 castor oil to which the invention is particularly suited is commercially available under the tradename Cremophor EL. Other polyethoxylated castor oils, such as Cremophor RH60, can be purified in a like manner.

In accordance with the process of the invention, the solvent is first dissolved to adjust viscosity. Preferably the solvent is dissolved in an alcohol, such as ethanol. In the preferred process, one liter of dehydrated ethanol is added for every kilogram of solvent to be purified and mixed to form a solution. The solvent-alcohol solution is then first contacted with an activated carbon column. Activated carbon is a porous network of carbon and is generally neutral in charge. Once thermally activated the carbon material is hygroscopic and absorbs water. The activated carbon removes impurities from the solvent that are believed to be unsaturated aliphatic and aromatic compounds. Measurement of the iodine value before and after treatment with activated carbon results in a drop in iodine value and is generally known by those skilled in the art as an indication that unsaturated compounds have been removed. The activated carbon is believed to function as an adsorbent with respect to these colored impurities. Suitable carbon columns would be apparent to those of ordinary skill in the art in view of the present disclosure and are commercially available. Preferred charcoal for use in the invention includes Darco GTS 12x4 and Norit GAC 1240 plus, commercially available from American Norit.

In carrying out the invention, the polyethoxylated castor oil solvent is contacted with the activated carbon column at a rate of from about 0.16 to 0.22 column volumes per hour (cv/hr), and still more preferably at a rate of 0.20 cv/hr. The preferred ratio of activated carbon to solvent is 0.2 Kg of activated carbon per Kg of polyethoxylated castor oil. Thus, in the preferred embodiment, employing a column volume of approximately 16 liters (8 kg of activated carbon), this yields from about 2.6 to about 4.8 liters per hour. Thus, the residence time for 1 liter is about 3.3 to 6.2 hours. As noted, if the amount of activated carbon is increased, then the flow rate should be increased so that total time spent on the column produces the desired result. Suitable amounts and flow rates to obtain the desired product, in particular the iodine value, can be readily empirically determined by one of ordinary skill in the art in view of the present invention.

The initial carbon treatment is followed by contacting the solvent with an ion exchange resin. In carrying out the preferred embodiment the eluent is pumped from the activated carbon column into a stainless steel holding tank prior to introduction to the ion exchange column. Preferably the solution is eluted through an ion exchange column at a rate of 0.12 to 0.30 cv/hour. The preferred ratios of the weight of the resin used to the polyethoxylated castor oil are between 0.21 to 0.22 Kg of resin per Kg of polyethoxylated castor oil. Suitable ion exchange resins for use in the process of the invention are commercially available from Amberlite and Dow Chemical and will be apparent to those of ordinary skill in the art in view of the present disclosure.

A preferred ion exchange resin for use in the invention is a mixed bed ion exchange resin, such as Amberlite MB 150. Preferably, the mixed bed ion exchange comprises an OH− type ion exchange resin and a H+ type ion exchange resin. The OH− type ion exchange resin exchanges OH− for carboxylate anions and other anions present in the solvent. Likewise, the H+ type ion exchange resin exchanges H+ for potassium and other cations present. The removal of the carboxylate anions is especially preferred since it is believed that the presence of carboxylate anions in the solvent reduces stability and shelf-life of certain pharmaceutical agents, such as paclitaxel. Advantageously, the use of inventive process does not affect solvent pH. Thus, in the preferred embodiment, using a column volume of about 11 liters of resin (8.6 Kg), this yields about 1.3 to 3.3 liters per hour of clean solvent having no change in pH before and after treatment. Thus, the preferred residence time per liter is approximately 3.3 to 8.5 hours.

Once the processing through the resin column is complete, the solution is then subjected to rotary evaporation to eliminate residual water and alcohol. Other means suitable for removing residual water and alcohol, such as climbing film evaporators and the like, will also be apparent to those of ordinary skill in the art in view of the instant disclosure.

The resulting purified polyethoxylated castor oil in one embodiment, such as for polyoxyl 35 castor oil, will have a specific gravity of between 1.05 and 1.06 g/ml, a viscosity between 650 and 850 cps at 25° C., an acid value (NF) of not more than 2.0, an hydroxyl value (NF) between 65 and 80, an iodine value (NF) between 25 and 35, a potassium content less than or equal to 15 ppm, a saponification value between 60 and 75 and a water content less than or equal to 0.5%.

The resulting purified solvent in another embodiment, such as for polysorbate 80, will have a specific gravity of between 1.06 and 1.09 g/ml, a viscosity between 300 and 500 cps, an acid value (NF) of not more than 2.2, a hydroxyl value (NF) between 65 and 80, a saponification value between 45 and 55 and a water content less than or equal to 3.0%.

The resulting purified polyethoxylated castor oil in another embodiment, such as for Cremophor RH60, will have a specific gravity of about 1.1 g/ml, a viscosity of about 211 cps at 60° C., an acid value (NF) of less than about 0.2, an iodine value (NF) less than 2, a potassium content about 7 ppm, a saponification value of about 44 and a water content about 0.4%.

While not bound by theory, it has been found that residence times above and below the specific ranges recited for the respective charcoal and resin ratios produce lower quality polyethoxylated castor oil products having inferior value as solvents in the preparation of injectable compositions containing pharmaceutical agents. The inventive process provides a polyethoxylated castor oil that can be defined by specific values for various impurities. These purified solvents when combined with pharmaceutical agents produce the stability necessary for longer shelf-life and minimal degradation of the pharmaceutical agent.

The purified solvent prepared by the process of the present invention has, among others, reduced overall content of potassium, anion and cation impurities, acid values and water giving a pure polyethoxylated castor oil. The following non-limiting examples and the associated tables are intended to demonstrate the preferred embodiments of the invention. One skilled in the art will recognize that numerous embodiments of the invention can be practiced to achieve the purified solvent and the stabilizing effect according to the invention.

EXAMPLE 1

The ion exchange resin was prepared by adding Amberlite MB-150 mixed bed ion exchange resin (19 lbs) and endotoxin free water (20 L) to a depyrogenated bin. To this, acetone (20 L) was added and stirred gently and intermittently for 20 minutes with a depyrogenated paddle. The resin was allowed to settle and the supernatant decanted and then discarded. The resin was washed in the same manner with endotoxin free water (15 L) until the absorbance in a 1 cm cell of the supernatant at 254 nm was less than 2. The supernatant was again decanted and discarded. The resin was resuspended in 20 L of dehydrated ethyl alcohol (USP) and mixed intermittently and gently. After allowing the resin to settle, the supernatant was discarded and the alcohol wash repeated. Dehydrated ethyl alcohol (USP, 20 L), was added to the washed resin, mixed and left to stand over night. The supernatant was discarded and the resin scooped into a column, cleaned with dehydrated ethyl alcohol (USP) and washed with alcohol until the effluent uv spectrum showed no absorbance greater than 0.05 between 220 to 400 nm relative to an alcohol blank. The foregoing provided a resin column volume of approximately 11 liters (15.2×61 cm).

Next, in a cleaned, rinsed chromatographic bin was placed Darco GTS 12×40 charcoal. Dehydrated ethyl alcohol (USP, 20 L) was added. The solution was stirred gently with a paddle. The charcoal was poured into a column and rinsed with alcohol until there were no carbon fines in the effluent and the uv spectrum showed no absorbance > than 0.05 between 220 to 400 nm relative to an alcohol blank. This provided a carbon column volume of approximately 16 liters (15.2×87.6 cm).

In a stainless steel tank 40 Kg of Cremophor EL and 40 L dehydrated ethyl alcohol were mixed until a uniform solution was obtained. The Cremophor EL/alcohol solution was then pumped at room temperature through the activated carbon column at a rate of 0.21 cv/hr. The first column volume was discarded and thereafter the effluent was collected in a stainless steel bin. The collected effluent was pumped through the Amberlite resin at a rate of 0.21 cv/hr at room temperature and the effluent collected. Again, the first column volume was discarded. The effluent collected after passing through both columns was filtered in an endotoxin free filter and collected in a depyrogenated container.

The filtered polyethoxylated castor oil was loaded on to a clean pyrogen free rotary evaporator and concentrated to remove alcohol. The concentrated polyethoxylated castor oil was filtered and assayed for residual water and alcohol content. The characteristics of the final product, which was then ready for use, are set forth in Table 1.

EXAMPLE 2

Example 2 was produced using the same process as set forth in example 1, except that the amount of Cremophor EL used was 12 Kg. All other parameters were scaled accordingly. However, for example 2 the charcoal column was eluted at a rate of 0.22 column volumes per hour and the Amberlite column was eluted at a rate of 0.22 column volumes per hour.

EXAMPLE 3

Example 3 was produced using the same process as set forth in example 1 except that 42 kg of Cremophor EL and 42 1 of dehydrated ethyl alcohol were used. However, for example 3 the flow rate for the charcoal column was varied from 0.23 to 0.62 column volumes per hour. Likewise, the Amberlite column was eluted at a varying rate from 0.33 to 0.90 column volumes per hour. As can be seen, under these process parameters, the resulting solvent composition had too much potassium. About 1.8 Kg of this material was then combined with 1.8 liters of dehydrated ethyl alcohol and run through a 500 ml Amberlite ion exchange column at a slower rate of 0.12 cv/hour The excess potassium of the resulting composition, shown as Example 3A in Table 1, was removed without adversely affecting the other composition parameters. This demonstrates that the mixed bed ion exchange resin can be run at a slower flow rate and that, by compensating with the use of more resin per kilogram of polyethoxylated castor oil, one can obtain the desired product.

COMPARATIVE EXAMPLE 4

Example 4 was produced using the same process as set forth in example 1. However, for example 4, 40.5 Kg of Cremophor EL was combined with 40.5 liters of dehydrated ethyl alcohol and run through the columns at altered flow rates. The charcoal column was eluted at a rate of 0.11 column volumes per hour. The Amberlite column was eluted at a rate of 0 17 column volumes per hour. As seen in Table 1, the iodine value resulting from this process was outside the acceptable limit.

COMPARATIVE EXAMPLE 5

Example 5 was produced using the same process as set forth in example 4. In this example the charcoal column was eluted at a -rate of 0.07 column volumes per hour and the Amberlite column was eluted at a rate of 0.11 column volumes per hour. As seen in Tables 1 and 2, the resulting solvent did not meet the acceptable limits for viscosity. While not being bound by theory, it is believed that this is because the solution was eluted at a considerably slower rate than that of the present invention.

COMPARATIVE EXAMPLE 6

Example 6 was produced using the same process as set forth in example 1. In this example, the charcoal column was eluted at a rate of 0.14 column volumes per hour and the flow rate for the Amberlite column was 0.22 column volumes per hour. As seen in Table 1, and as with example 4, the iodine value resulting from this process was outside the acceptable limit. It is believed that in each instance this is due to low flow rates through the charcoal column.

EXAMPLE 7

Example 7 was produced using the same process as set forth in example 1. However, the charcoal column was eluted at varying flow rates from 0.16 to 0.225 columns per hour. Similarly, the Amberlite column was eluted at a varying rate from 0.12 to 0.15 columns per hour.

EXAMPLE 8

In this example, a mixture of several batches of polyoxyl 35 castor oil purified according to the process of example 1 was prepared. The lots of polyoxyl 35 castor oils used in examples 1, 2 and 7 were mixed in the amounts of 10 Kg, 12 Kg and 12 Kg, respectively. As would be expected, and as seen in Table 1, mixing these three batches resulted in a product falling within the desired parameters. This composition was used to prepare the stabilized pharmaceutical composition described in association with Table 3.

EXAMPLES 9–11

In these examples, about 4 kg of the same lot of polyoxyl 35 castor oil was purified according to the process of example 1. The amount of charcoal was varied from 0.1 kg charcoal per kg of polyoxyl 35 castor oil to 0.4 kg charcoal per kg of polyoxyl 35 castor oil. As seen in Table 1, the results from this process were within the acceptable limits for each example.

EXAMPLE 12

In this example, about 4 kg of polysorbate 80 was purified according to the process of example 1. All other parameters were adjusted accordingly. The characteristics of the final product, which was then ready for use, are set forth in Table 4.

EXAMPLE 13

In this example, about 4 kg of Cremophor RH60 was purified according to the process of example 1. All other parameters were adjusted accordingly. The characteristics of the final product, which was then ready for use, are set forth in Table 5.

TABLE 1

SUMMARY OF ANALYTICAL DATA: CLEANED POLYOXYL 35 CASTOR OIL

| lot or batch number | specific gravity | viscosity (cpa) | acid value | hydroxyl value | iodine value | saponification value | potassium (ppm) | % water |
|---|---|---|---|---|---|---|---|---|
| Acceptable limits | 1.05–1.06 | 650–850 435–565[1] | not more than 2.0 | 65–80 | 25–35 | 60–75 | <=15 ppm | ≦0.5% |
| Cremophor EL (starting material) | 1.06 | 757 | 0.4 | 70 | 33 | 66 | 404 | 2.5 |
| Example 1 | 1.06 | 780 | 0.14 | 79.8 | 30.8 | 61.5 | 12 | 0.071 |
| Example 2 | 1.06 | 694 | 0.07 | 74.5 | 30 | 69.7 | <10 | <0.19 |
| Example 3 | 1.06 | 753 | 0.1 | 74.1 | 28.3 | 67 | 19 | 0.0643 |
| Example 3A | 1.06 | 847 | 0.12 | 69.6 | 32 | 71.5 | 4 | 0.031 |
| Example 4 | 1.06 | 757.3 | 0.08 | 73.1 | 23 | 63.1 | <10 | <0.17 |
| Example 5 |  | 636 |  |  |  |  |  | 0.121 |
| Example 6 | 1.06 | 687 | 0.08 | 69.1 | 19 | 64 | <10 | <0.18 |
| Example 7 | 1.06 | 657 | 0.07 | 68.3 | 31.8 | 65.4 | <5 | 0.053% |
| Example 8 | 1.06 | 678 | 0.2 | 72 | 27.8 | 61 | 6.6 | 0.25% |
| Example 9 | 1.05 | 483[1] | 0.13 | 75.7 | 34.55 | 64.9 | <5 | 0.14% |
| Example 10 | 1.053 | 491[1] | 0.1 | 77.9 | 33.15 | 63.5 | <5 | 0.13% |
| Example 11 | 1.053 | 470[1] | 0.15 | 74.1 | 32.88 | 61.4 | <5 | 0.15% |

[1]Viscosity determined at 30° C.

Table 2 shows the specific ratios of charcoal and Amberlite per Kg of polyethoxylated castor oil and the flow rate used for each.

TABLE 2

CHROMATOGRAPHY DATA: CLEANED POLYOXYL 35 CASTOR OIL

| lot or batch number | Amount of Cremophor (Kilograms) | Kg of charcoal per Kg Cremophor | flow rate charcoal column (cv/hr) | Kg of ion exchange resin per Kg Cremophor | flow rate ion exchange column (cv/hr) |
|---|---|---|---|---|---|
| Example 1 | 40 | 0.2 | 0.21 | 0.22 | 0.3 |
| Example 2 | 24 | 0.2 | 0.22 | 0.21 | 0.28 |
| Example 3 | 42 | 0.19 | 0.23–0.62 | 0.2 | 0.33–0.90 |
| Example 3A | 1.8 |  |  | 0.38 | 0.12 |
| Example 4 | 40.5 | 0.2 | 0.11 | 0.21 | 0.17 |
| Example 5 | 40.5 | 0.2 | 0.07 | 0.21 | 0.11 |
| Example 6 | 40 | 0.2 | 0.14 | 0.22 | 0.22 |
| Example 7 | 40 | 0.2 | 0.16–0.26 | 0.22 | 0.12–0.15 |
| Example 8 | 34 | 0.2 | 0.21 | 0.22 | 0.3 |
| Example 9 | 4 | 0.1 | 0.19 | 0.19 | 0.14 |
| Example 10 | 4.2 | 0.19 | 0.24 | 0.19 | 0.20 |
| Example 11 | 4 | 0.4 | 0.2 | 0.2 | 0.22 |

As shown in Table 3, the stability of a composition of Paclitaxel and polyethoxylated castor oil is dramatically improved when the process of the present invention is

TABLE 3

STABILITY OF PACLITAXEL IN POLYOXYL 35 CASTOR OIL/ETHANOL SOLUTION
Content of Paclitaxel (percent of formulation)

| Time of Storage | Solution Prepared with Cleaned Polyoxyl 35 Castor Oil | | | Solution Prepared with Cremophor EL | | |
|---|---|---|---|---|---|---|
|  | Stored at 27.5° C. | Stored at 40° C. | Stored at 50° C. | Stored at 27.5° C. | Stored at 40° C. | Stored at 50° C. |
| Initial | 102.0% | 102.0% | 102.0% | 100.5% | 100.5% | 100.5% |
| 1 month | 101.9% | 101.6% | 100.9% | 97.0% | 81.0% | 50.4% |
| 2 months | 101.7% | 99.9% | 100.4% | 92.0% | 66.1% | 28.8% |
| 3 months | 99.1% | 97.8% | 98.0% | 87.8% | 55.5% | 16.7% |

The process according to the invention, and product parameters described herein, result in a polyethoxylated castor oil solvent or solubilizing agent that enables the preparation of advantageously stable pharmaceutical compositions.

employed to prepare the solvent. The values reported in Table 3 were obtained by dissolving the paclitaxel in Cremophor and dehydrated ethyl alcohol. After filtration formulation vials were filed with 5.5 ml of the composition and sealed. The vials were then maintained at between 25.5–29.5, 38–42 and 48–52° C., with the target temperatures being 27.5, 40 and 50° C., respectively. The vials were assayed initially and at approximately one, two and three month intervals, to give the percent paclitaxel remaining based upon 100% (±5) initial value.

These results depict the important and unexpectedly superior improvements made by the present invention. At all of the temperatures tested and for all months of storage tested, when the paclitaxel was mixed with polyethoxylated castor oil prepared pursuant to the present invention, there were significant decreases in degradation.

TABLE 4

SUMMARY OF ANALYTICAL DATA: CLEANED POLYSORBATE 80

| lot or batch number | specific gravity | viscosity (cps) | acid value | hydroxyl value | saponification value | % water |
|---|---|---|---|---|---|---|
| Acceptable limits | 1.06–1.09 | 300–500 | not more than 2.2 | 65–80 | 45–55 | ≦3.0% |
| Example 12 | 1.08 | 391 | 0.08 | 79.8 | 46 | 0.14% |

Shown in Table 4 are the results using the inventive process with polysorbate 80 solvent. Polysorbate 80, also referred to as Tween 80, is approved for internal use by the Food and Drug Administration as a dispersing agent for pharmaceutical agents. The National Formulary sets the acceptable limits allowed for polysorbate 80 if it is to be used as a dispersant for pharmaceutical agents. Polysorbate 80 is a non-ionic surfactant and can generally be classified as a polyol with a similar chemical structure to polyoxyl 35 castor oil. As discussed above, certain pharmaceutical agents degrade in the presence of carboxylate anions and other impurities. Thus, for example, a low acid number is desired for increased stability and shelf life. Processing polysorbate 80 according to the present invention results in a low acid number of a 0.08.

TABLE 5

SUMMARY OF ANALYTICAL DATA: CLEANED CREMOPHOR RH60

| lot or batch number | specific gravity | viscosity (cps) | acid value | iodine value | potassium (ppm) | hydroxyl value | saponification value | % water |
|---|---|---|---|---|---|---|---|---|
| Example 13 | 1.10 | 211 @ 60° C. | less than 0.2 | less than 0.2 | <7 | 69 | 44 | 0.4 |

Shown in Table 5 are the results using the inventive process with Cremophor RH60 solvent. Cremophor RH60 is similar in structure to Cremophor EL and has about 60 ethoxy linkages compared to about 23 ethoxy linkages for Cremophor EL. Additionally, Cremophor RH60 is substantially fully hydrogenated. Results indicate that Cremophor RH60 purified according to the present invention has very low impurity levels.

The foregoing description of the preferred embodiments of the invention has been presented for purposes of illustration and description. It is not intended to be exhaustive or to limit the invention to the precise forms disclosed. Obvious modifications or variations are possible in light of the above teachings. The embodiments were chosen and described to provide the best illustration of the principles of the invention and its practical applications to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A process for purifying a non-ionic solvent comprising the steps of:
   (a) forming a solution of said solvent and alcohol;
   (b) contacting the solution with activated carbon;
   (c) contacting the solution with an ion exchange resin; and
   (d) evaporating residual water and alcohol;
   whereby said solvent is adapted to produce a stabilized pharmaceutical composition.

2. The process according to claim 1 wherein said step of forming said solution comprises forming a solution of polyethoxylated castor oil and alcohol.

3. The process according to claim 1 wherein said step of forming said solution comprises mixing about one liter of alcohol for every kilogram of polyethoxylated castor oil.

4. The process according to claim 1 wherein said solvent is a polyethoxylated castor oil and step of contacting said solution with activated carbon comprises contacting said solution with said activated carbon in a carbon column at a rate wherein one liter of said polyethoxylated castor oil will be in contact with said carbon for between about 3.3 to about 6.2 hours.

5. The process according to claim 1 wherein said solvent is a polyethoxylated castor oil and said step of contacting said solution with an ion exchange resin comprises contacting said solution with a mixed bed ion exchange resin in a resin column at a rate wherein one liter of polyethoxylated castor oil will be in contact with said resin for not less than about 3.3 hours.

6. The process according to claim 1 wherein said solvent is a polyethoxylated castor oil and said step of contacting said solution with an ion exchange resin comprises contacting said solution with a mixed bed ion exchange resin in a resin column at a rate wherein one liter of polyethoxylated castor oil will be in contact with said resin for between about 3.3 and 8.5 hours.

7. The process according to claim 1 wherein the solvent is a polyoxyl-35 castor oil.

8. The process according to claim 1 wherein the solvent is a polysorbate 80.

9. The process according to claim 1 wherein the solvent is a Cremophor RH60.

10. The process according to claim 1 wherein said solvent is polyoxyl-35 castor oil and steps are carried out to produce a polyethoxylated castor oil having a specific gravity of between about 1.05 and 1.06 g/ml, a viscosity of between about 650 and 850 cps, an acid value of not more than about 2.0, a hydroxyl value of between about 65 and 80, an Iodine value of between about 25 and 35, a saponification value of between about 60 and 75, not more than about 15 ppm potassium, and not more than about 0.5% water.

11. The process according to claim 1 wherein said solvent is polysorbate 80 and steps are carried out to produce polysorbate 80 having a specific gravity of between about 1.06 and 1.09 g/ml, a viscosity of between about 300 and 500 cps, an acid value of not more than about 2.2, a hydroxyl value of between about 65 and 80, a saponification value of between about 45 and 55, and less than about 3.0% water.

12. The process according to claim 1 wherein said solvent is polyethoxylated castor oil and said steps are carried out to produce a solvent adapted to produce, when combined with paclitaxel, a pharmaceutical composition comprising at least about 90% of the initial amount of paclitaxel, after being stored at 40° C. for ninety days upon admixture therewith.

13. A process for purifying a polyoxyl 35 castor oil solvent comprising contacting the solvent with activated carbon and contacting the solvent with an ion exchange resin in an amount and for a duration sufficient to produce the polyoxyl 35 castor oil having a specific gravity of between about 1.05 and 1.06, a viscosity of between about 650 and 850 cps, an acid value of not more than about 2.0, a hydroxyl value of between about 65 and 80, an Iodine value of between about 25 and 35, a saponification value of between about 60 and 75, not more than about 15 ppm potassium, and not more than about 3.0% water, whereby said solvent is adapted to produce a stabilized pharmaceutical composition.

14. A process for purifying a polyoxyl 35 castor oil solution comprising contacting the solution with activated carbon and contacting the solution with an ion exchange resin in an amount and for a duration sufficient to produce a polyoxyl 35 castor oil adapted to produce, when combined with paclitaxel, a pharmaceutical composition comprising at least about 90% of the initial amount of paclitaxel after being stored at 40° C. for ninety days upon admixture therewith.

15. A solvent produced by the process according to claim 1, 13 or 14.

16. A stabilized pharmaceutical composition comprising a solvent containing a purified polyethoxylated castor oil according to claim 1, 13 or 14 and a pharmaceutical agent.

17. The composition of claim 13 wherein the pharmaceutical agent is selected from the group consisting of an antineoplastic agent, an immunosuppressive agent, an antifungal agent, an oil soluble vitamin or mixture thereof.

18. The composition of claim 13 wherein said solvent further comprises an alcohol.

19. A stabilized pharmaceutical composition comprising a solvent containing a purified polyethoxylated castor oil according to claim 1, 13 or 14 and paclitaxel, said composition comprising at least about 90% of the initial amount of paclitaxel after being stored at 40° C. for 90 days.

20. A process for purifying a non-ionic solvent comprising the steps of:
  (a) contacting the solvent with activated carbon;
  (b) contacting the solvent with an ion exchange resin; and
    whereby said solvent is adapted to produce a stabilized pharmaceutical composition.

21. The process for purifying a non-ionic solvent according to claim 20 further comprising the step of adding a viscosity modifier to the solution for lowering the viscosity prior to step (a).

22. The process for purifying a non-ionic solvent according to claim 20 wherein said viscosity modifier is an alcohol.

23. A process for purifying a polyethoxylated castor oil comprising the steps of
  a.) forming a solution of the polyethoxylated castor oil and an alcohol;
  b.) adsorbing water and unsaturated aliphatic and aromatic compounds from said solution;
  c.) exchanging anions and cations other than H+ and OH− from said solution with H+ and OH−; and
  d.) evaporating said alcohol from said solution.

24. The process according to claim 23 wherein a pH of said solution remains about the same during steps (a–d).

25. A process for purifying a polyethoxylated castor oil comprising exchanging carboxylate anions from the castor oil with OH− wherein said carboxylate anions are removed from the castor oil whereby the castor oil is adapted to produce a stabilized pharmaceutical composition.

26. The process according to claim 25 wherein said polyethoxylated castor oil is polyoxyl 35 castor oil.

27. A process for stabilizing a pharmaceutical composition comprising a solvent containing a polyethoxylated castor oil having carboxylate anions and a pharmaceutical agent, said method comprising the steps of exchanging carboxylate anions from the polyethoxylated castor oil with OH−; and dissolving the pharmaceutical agent in the castor oil to produce the stabile pharmaceutical composition.

28. The process according to claim 27 wherein said pharmaceutical agent is paclitaxel, wherein said composition comprises at least about 90% of the initial amount of paclitaxel after being stored at 40° C. for 90 days.

* * * * *